Nov. 26, 1963 W. ZOMBORY ETAL Plant Pat. 2,320
DIANTHUS PLANT
Filed Oct. 9, 1962
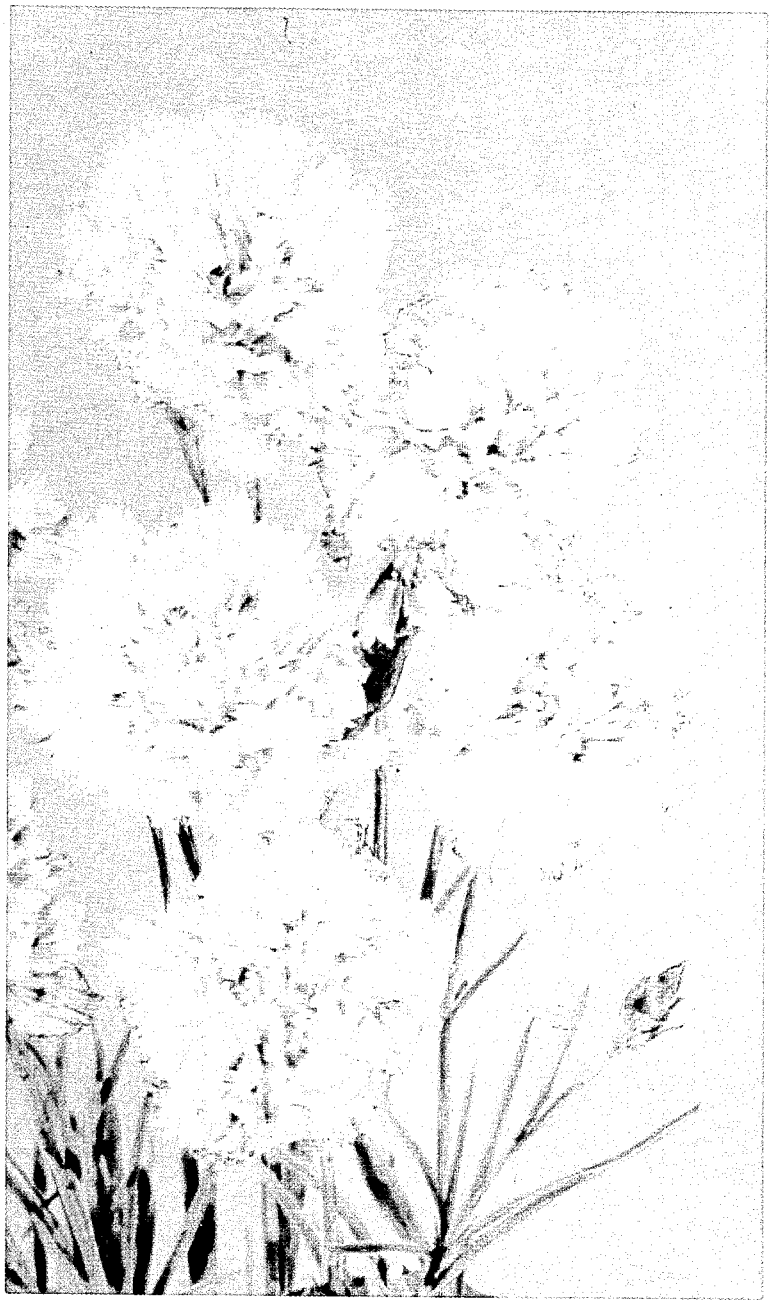
Inventors.
William Zombory and
Sophia B. Zombory
By: Robb & Robb
Attorneys.

United States Patent Office

Plant Pat. 2,320
Patented Nov. 26, 1963

2,320
DIANTHUS PLANT

William Zombory and Sophia B. Zombory, Detroit, Mich., assignors to Jackson & Perkins Company, Newark, N.Y., a corporation of New York Filed Oct. 9, 1962, Ser. No. 229,513
1 Claim. (Cl. Plt.—71)

The present invention relates to a new and distinct variety of dianthus plant, which was originated by us by crossing the variety known as "Caprice" (Plant Patent No. 1,851) with an unnamed and unpatented seedling of unidentified origin.

The primary objective of this breeding was to produce a new dianthus variety which begins to bloom the first year and blooms continuously throughout the season, and which is hardy and bears flowers of a color different from that of the parent variety "Caprice." This objective was fully achieved, along with other desirable improvements, as evidenced by the following unique combination of outstanding characteristics which distinguish our new variety from its parents, as well as from all other varieties of which we are aware:

(1) Hardy and upright habits of growth;

(2) A habit of commencing to bloom the first year from cuttings;

(3) A continuous blooming habit throughout the season;

(4) A large flower size; and (5) A distinctive and attractive general color tonality of the flower corresponding to Spinel Red, lightly overcast with Spinel Pink in the lower half of the flower petals, while being Spinel Pink, lightly overcast with Thulite Pink in the upper half of the flower petals.

Asexual reproduction of our new variety by cuttings, as performed at Detroit, Michigan, and also at Newark, New York, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with Ridgway's Color Standards and Nomenclature:

Parentage: Seedling.

*Seed parent.*—"Caprice."

*Pollen parent.*—An unnamed seedling of unidentified origin.

Blooming season: Starts blooming the first year from cuttings, with blooms during June and July and again during September and October.

*Plant*

Growth: Medium tall (about 12 inches); compact; upright; cespitose perennial; sends up flowering shoots the first year.

Leaves: Many bottom leaves in tufts; from 2¾ inches to 3 inches long; narrow; thick. Color—Bice Green, Plate 17, overcast with a silvery sheen of Yellowish Glaucous, Plate 41.

Flower stems: About 12 inches long; strong; nodes prominently swollen and partially covered in the leaf sheath; from 2 to 4 flowers per stem, but usually 3 flowers. Color—Light Bice Green, Plate 17.

*Flowers*

Borne: Mostly on own-branched stalks, but some of the laterals nearly sessile.

Size: 2 inches in diameter at first, with later flowers on laterals ranging from 1¼ inches to 1¾ inches in diameter.

Petals: Average from 30 to 35 in number in fully grown flowers; about ¼ inch wide at the widest point; ranging up to ¾ inch long. Color—Spinel Red, Plate 26, lightly overcast with Spinel Pink, Plate 26 over lower half of petals, and Spinel Pink, Plate 26, lightly overcast with Thulite Pink, Plate 26 over upper half of petals, with a small blotch of Bordeaux color, Plate 12 at the throat, and a claw of White, Plate 53 blended in with Glass Green, Plate 31.

Calyx: Cylindrical; about ¾ inch long; erect; small teeth; splits on wide open flowers. Color—teeth of Courge Green, Plate 17, with lower half of calyx lightly overcast with Bordeaux, Plate 12.

Bracts: 4 in number; small. Color—Absinthe Green, Plate 31, edged with Indian Lake, Plate 26.

Stamens: About 12 in number; about 1 inch long. Color—White, Plate 53.

Anthers: Color—Light Pinkish Lilac, Plate 37.

Ovary: Small; oval.

Fragrance: Very sweet and strong. Nature—Strong Old Spice.

We claim:

A new and distinct variety of dianthus plant, substantially as herein shown and described, characterized particularly as to novelty by the unique combination of hardy and upright habits of growth, a habit of commencing to bloom the first year from cuttings, a continuous blooming habit throughout the season, a large bloom size, and a distinctive and attractive general color tonality of the flowers corresponding to Spinel Red, lightly overcast with Spinel Pink over the lower half of the flower petals, and Spinel Pink, lightly overcast with Thulite Pink over the upper half of the flower petals.

No references cited.